(12) United States Patent
Buchheister et al.

(10) Patent No.: US 11,678,979 B2
(45) Date of Patent: Jun. 20, 2023

(54) EYE IMPLANT FOR AN ACCOMMODATIVE INTRAOCULAR LENS

(71) Applicant: Carl Zeiss Meditec AG, Jena (DE)

(72) Inventors: Jan Buchheister, Jena (DE); Stefan Troeger, Stützengrün (DE); André Wolfstein, Berlin (DE); Hristina Srbinoska, Kleinmachnow (DE); Almut Czap, Aalen (DE)

(73) Assignee: CARL ZEiSS MEDITEC AG, Jena (DE)

( * ) Notice: Subject to any disclaimer, the term of this patent is extended or adjusted under 35 U.S.C. 154(b) by 0 days.

(21) Appl. No.: 17/784,049

(22) PCT Filed: Dec. 4, 2020

(86) PCT No.: PCT/EP2020/084692
§ 371 (c)(1),
(2) Date: Jun. 9, 2022

(87) PCT Pub. No.: WO2021/115964
PCT Pub. Date: Jun. 17, 2021

(65) Prior Publication Data
US 2023/0016874 A1   Jan. 19, 2023

(30) Foreign Application Priority Data
Dec. 12, 2019   (DE) ..................... 10 2019 134 169.8

(51) Int. Cl.
*A61F 2/16*   (2006.01)
(52) U.S. Cl.
CPC .... *A61F 2/1694* (2013.01); *A61F 2002/1682* (2015.04)

(58) Field of Classification Search
CPC ....................... A61F 2/1694; A61F 2002/1682
See application file for complete search history.

(56) References Cited

U.S. PATENT DOCUMENTS

| 4,327,171 A | 4/1982 | Poler |
| 5,002,571 A | 3/1991 | O'Donnell, Jr. et al. |

(Continued)

FOREIGN PATENT DOCUMENTS

| CN | 106999277 A | 8/2017 |
| CN | 109789241 A | 5/2019 |

(Continued)

OTHER PUBLICATIONS

Written Opinion of the International Searching Authority for PCT/EP2020/084692 dated Mar. 18, 2021 (7 pages).

(Continued)

*Primary Examiner* — Javier G Blanco
(74) *Attorney, Agent, or Firm* — Alston & Bird LLP

(57) ABSTRACT

Provided is an eye implant having a lens sheath which is embodied for insertion in a capsular bag of an eye, is elastic, delimits a cavity in its interior and has a through hole via which the cavity is accessible from outside of the lens sheath, a plurality of reservoirs which are fastened to the lens sheath, project from the lens sheath to the outside, have an adhesive in their interior and are embodied to dispense the adhesive when pressed against the capsular bag, and at least two adapters which are fastened to the lens sheath, project from the lens sheath into the interior, and are embodied to engage with a respective haptic of an accommodative intraocular lens.

5 Claims, 4 Drawing Sheets

(56) References Cited

U.S. PATENT DOCUMENTS

| | | | |
|---|---|---|---|
| 5,098,444 | A | 3/1992 | Feaster |
| 10,052,197 | B2 | 8/2018 | Dolla et al. |
| 10,327,889 | B2 | 6/2019 | Honigsbaum |
| 2005/0251253 | A1 | 11/2005 | Gross |
| 2011/0029074 | A1 | 2/2011 | Reisin et al. |
| 2016/0000558 | A1 | 1/2016 | Honigsbaum |
| 2019/0269499 | A1 | 9/2019 | Ellis |

FOREIGN PATENT DOCUMENTS

| | | |
|---|---|---|
| WO | WO 2011/085349 A2 | 7/2011 |
| WO | WO 2017/030582 A1 | 2/2017 |
| WO | WO 2017/221068 A1 | 12/2017 |

OTHER PUBLICATIONS

German Examination Report including Search for German Patent Application No. 10 2019 134 169.8, dated May 10, 2020 (16 pages).

International Search Report and Written Opinion for International Application No. PCT/EP2020/084692, dated Mar. 18, 2021 (16 pages).

Office Action including Search received for Chinese Patent Application No. 202080085783.1, dated Jan. 11, 2023 (11 pages).

EYE IMPLANT FOR AN ACCOMMODATIVE INTRAOCULAR LENS

CROSS-REFERENCE TO RELATED APPLICATIONS

The present application is a national phase entry of International Application No. PCT/EP2020/084692, filed Dec. 4, 2020, which claims priority to German Patent Application No. 10 2019 134 169.8, filed Dec. 12, 2019, which are incorporated herein by reference in their entirety.

The invention relates to an eye implant for an accommodative intraocular lens.

Accommodation is understood to mean the ability of the eye to dynamically adapt the refractive power and as a result see objects at different distances in focus. In the process, a change in diameter of a ciliary muscle in the eye is transferred via zonular fibers to a flexible capsular bag, within which a flexible lens is arranged. However, the ability to accommodate deteriorates with increasing age, having presbyopia as a consequence. This is predominantly due to a reducing elasticity of the lens, which solidifies with increasing age. An accommodative intraocular lens that is deformable by the ciliary muscle is used to try to maintain the eye's ability to accommodate. However, none of the current accommodative intraocular lenses facilitate a sufficient force transfer from the ciliary muscle to the accommodative intraocular lens in order to facilitate accommodation.

It is therefore an object of the invention to develop an eye implant with which a force transfer from a ciliary muscle to an accommodative intraocular lens works well.

The first eye implant according to the invention has a lens sheath which is embodied for insertion in a capsular bag of an eye, is elastic, delimits a cavity in its interior and has a through hole via which the cavity is accessible from outside of the lens sheath, a plurality of reservoirs which are fastened to the lens sheath, project from the lens sheath to the outside, have an adhesive in their interior and are embodied to dispense the adhesive when pressed against the capsular bag, and at least two adapters which are fastened to the lens sheath, project from the lens sheath into the interior, and are embodied to engage with a respective haptic of an accommodative intraocular lens. The lens sheath may contain or consist of silicone and/or polyurethane. The material of the lens sheath or of the reservoirs may contain a shape-memory material. The reservoirs may contain or consist of silicone and/or polyurethane. By way of example, the reservoirs can be bubbles.

By way of example, the adhesive can be a "super adhesive" as described at https://www.berlin-university-alliance.de/impressions/20180110-mussel-based-super-adhesive/index.html. Alternatively, the adhesive can be what is known as a "tissue adhesive" or can be HLAA (hydrophobic light-activated adhesive) from Geck Biomedical, Paris, cf. https://www.deutsche-apotheker-zeitung.de/daz-az/2014/daz-3-2014/chirurgischer-klebstoff. It is also conceivable that the adhesive is a two-component adhesive. The two components of the two-component adhesive can be arranged in two separate chambers within the reservoir and can mix when the reservoirs are pressed against the capsular bag. Moreover, the adhesive can be elastic.

The second eye implant according to the invention has a lens sheath which is embodied for insertion in a capsular bag of an eye, is elastic, delimits a cavity in its interior and has a through hole via which the cavity is accessible from outside of the lens sheath, a plurality of protective sheaths which are fastened to the lens sheath and project from the lens sheath to the outside, a respective barb for each protective sheath, each barb being encapsulated in the interior of the associated protective sheath, being connected to the lens sheath, projecting from the lens sheath to the outside and being embodied to pierce the associated protective sheath and catch in the capsular bag when the barb is pressed against the capsular bag, and at least two adapters which are fastened to the lens sheath, project from the lens sheath into the interior, and are embodied to engage with a respective haptic of an accommodative intraocular lens.

The eye implant is provided to be inserted into the capsular bag of the eye after a surgeon performed phacoemulsification on the crystalline lens of the eye, the crystalline lens being comminuted and aspirated. The eye implant is inserted into the capsular bag when the cavity of the lens sheath is as empty as possible and the lens sheath consequently requires little space. The lens sheath is subsequently pumped up by virtue of an operating fluid being pressed into the cavity via the through hole by means of a cannula. To this end, it is conceivable for the through hole to be embodied to seal the cannula so that little operating fluid or no operating fluid can reach out of the cavity while the lens sheath is being pumped up. By virtue of being flexible, the lens sheath can adjust to various capsular bag sizes. The eye implant is fastened to the capsular bag by means of the adhesive or the barb. As a result of the provision of the reservoirs in accordance with the first eye implant according to the invention, the adhesive is kept within the reservoirs while the eye implant is inserted into the capsular bag, allowing the eye implant to be compressed and/or folded without the adhesive agglutinating the eye implant. By virtue of the eye implant being compressed and/or folded, the eye implant can be introduced into the capsular bag via only a small incision in the cornea. By way of example, it is conceivable that the eye implant is introduced via the same incision in the cornea of the eye, through which the crystalline lens was also aspirated. Analogously, the provision of the protective sheaths in accordance with the second eye implant according to the invention allows the eye implant to be compressed and/or folded without the barbs damaging the eye implant in the process. After the lens sheath was pumped up, the surgeon introduces an insertion opening into the lens sheath, for example by means of a blade or a pair of forceps. Subsequently, the accommodative intraocular lens is inserted into the lens sheath via the insertion opening and the surgeon causes each haptic to engage with one of the adapters in each case, as a result of which the accommodative intraocular lens is fastened to the eye implant. As the eye implant is fastened to the capsular bag, there is a good force transfer from a ciliary muscle of the eye to the eye implant. As the accommodative intraocular lens is fastened to the eye implant, there is a good force transfer from the eye implant to the accommodative intraocular lens, as a result of which there is a good overall force transfer from the ciliary muscle to the accommodative intraocular lens. In this case, the eye implant can be fastened to the capsular bag while the lens sheath is being pumped up and/or while the accommodative intraocular lens is being inserted into the lens sheath.

For the first embodiment according to the invention, it is preferable for the reservoirs to each have a predetermined breaking point which is embodied to be opened when the reservoirs are pressed against the capsular bag, or for the reservoirs to each have a reservoir opening which is embodied to allow the adhesive to pass when the reservoirs are pressed against the capsular bag.

For the first embodiment according to the invention, it is preferable for the lens sheath to have a sheath opening for each of the reservoirs and for one of the adapters which is in contact with the adhesive to be arranged at each of the sheath openings. When the haptics are in engagement with the respective one of the adapters, the adapter presses the adhesive onto the capsular bag. As a result, the eye implant advantageously can be fastened particularly securely to the capsular bag.

For the second embodiment according to the invention, it is preferable for each of the barbs to extend through the lens sheath and be fastened to one of the adapters. When the haptics are in engagement with the respective one of the adapters, the adapter presses the barb onto the capsular bag. As a result, the eye implant advantageously can be fastened particularly securely to the capsular bag. Moreover, the barb is particularly securely fastened by means of the adapter, in particular in comparison with the case where the barb would be only fastened to the lens sheath.

For the second embodiment according to the invention, it is preferable for the protective sheaths to be embodied to decompose following the insertion of the eye implant into the capsular bag.

For both embodiments according to the invention, it is preferable for the lens sheath to be discus-shaped. Advantageously, this shape of the lens sheath is easy to produce. Alternatively, it is preferable for the two embodiments according to the invention for the lens sheath to be toroidal. As a result, the lens sheath can advantageously have a space-saving embodiment. This is particularly relevant if it is compressed and/or folded in order to be inserted into the capsular bag. Moreover, it is possible to position the toroidal embodiment of the lens sheath into the beam path of the eye in such a way that little or no light which previously passed through the lens sheath is incident on the retina.

For both embodiments according to the invention, it is preferable for the lens sheath to have a lens sheath swelling arranged around the through hole. This can reduce a risk of damage to the lens sheath while the latter is pumped up. Particularly preferably, the lens sheath swelling is arranged to the outside of the lens sheath. As a result, it is possible to keep the cannula in a stable position within the lens sheath swelling while the operating fluid is pressed into the cavity.

For both embodiments, it is preferable for the lens sheath to comprise a valve which contains the through hole. In the case where the lens sheath swelling is provided, the lens sheath swelling can be arranged around the valve or be part of the valve.

For both embodiments, the lens sheath preferably has a predetermined sheath breaking point. The insertion opening can be produced particularly easily by opening the predetermined sheath breaking point. By way of example, the predetermined sheath breaking point can be a perforation. In the case where the lens sheath swelling is provided, the predetermined sheath breaking point can be arranged around the lens sheath swelling. As a result, the lens sheath swelling can be grasped by means of forceps for the purposes of producing the insertion opening.

Particularly preferably, two of the predetermined sheath breaking points provided opposite one another on the lens sheath are provided. As a result, the insertion opening can be produced independently of how the eye implant is arranged in the capsular bag.

For both embodiments, it is preferable for each of the adapters to comprise a first adapter arm and a second adapter arm which are embodied such that the haptic engages therebetween. By means of the first adapter arm and the second adapter arm, it is possible to stretch the capsular bag. In particular, this makes it possible to prevent the anterior region of the capsular bag and the posterior region of the capsular bag from contacting. Stretching the capsular bag allows both the probability of occurrence of a secondary cataract and the intensity of the secondary cataract to be reduced. By virtue of the capsular bag being stretched, the transformation and growth factors emitted by the equatorial cells are diluted by circulating aqueous humor. Then, fewer equatorial cells are converted into fibroblasts, as a result of which fibrosis is also reduced.

For both embodiments, it is preferable for the eye implant to have at least two magnets or magnetizable eye implant regions, which are embodied to each fasten one of the haptics to the eye implant. As a result, the intraocular lens can be fastened particularly securely to the eye implant. The magnets or the magnetizable eye implant regions can be arranged in the lens sheath and/or in the adapters. Should the magnets be provided, the haptics may have magnetizable haptic regions or magnets. Should the magnetizable eye implant regions be provided, the haptics may have magnets. It is conceivable for the magnets in the eye implant and/or in the haptics to be present in the form of magnetic nanoparticles.

The lens sheath preferably has a scale on its outer side in both embodiments. This renders the extent to which the lens sheath has been pumped up identifiable.

In both embodiments, the adapters are preferably configured in such a way that the intraocular lens is always able to have the same radial diameter independently of the size of the capsular bag.

In both embodiments, the operating fluid preferably contains a lubricant and/or a physiological saline solution or consists of the lubricant and/or the physiological saline solution. The lubricant can be an ophthalmic viscoelastic device (OVD).

A kit according to the invention comprises the eye implant and the accommodative intraocular lens.

The invention is explained in more detail below with reference to the appended schematic drawings.

Figure 1:
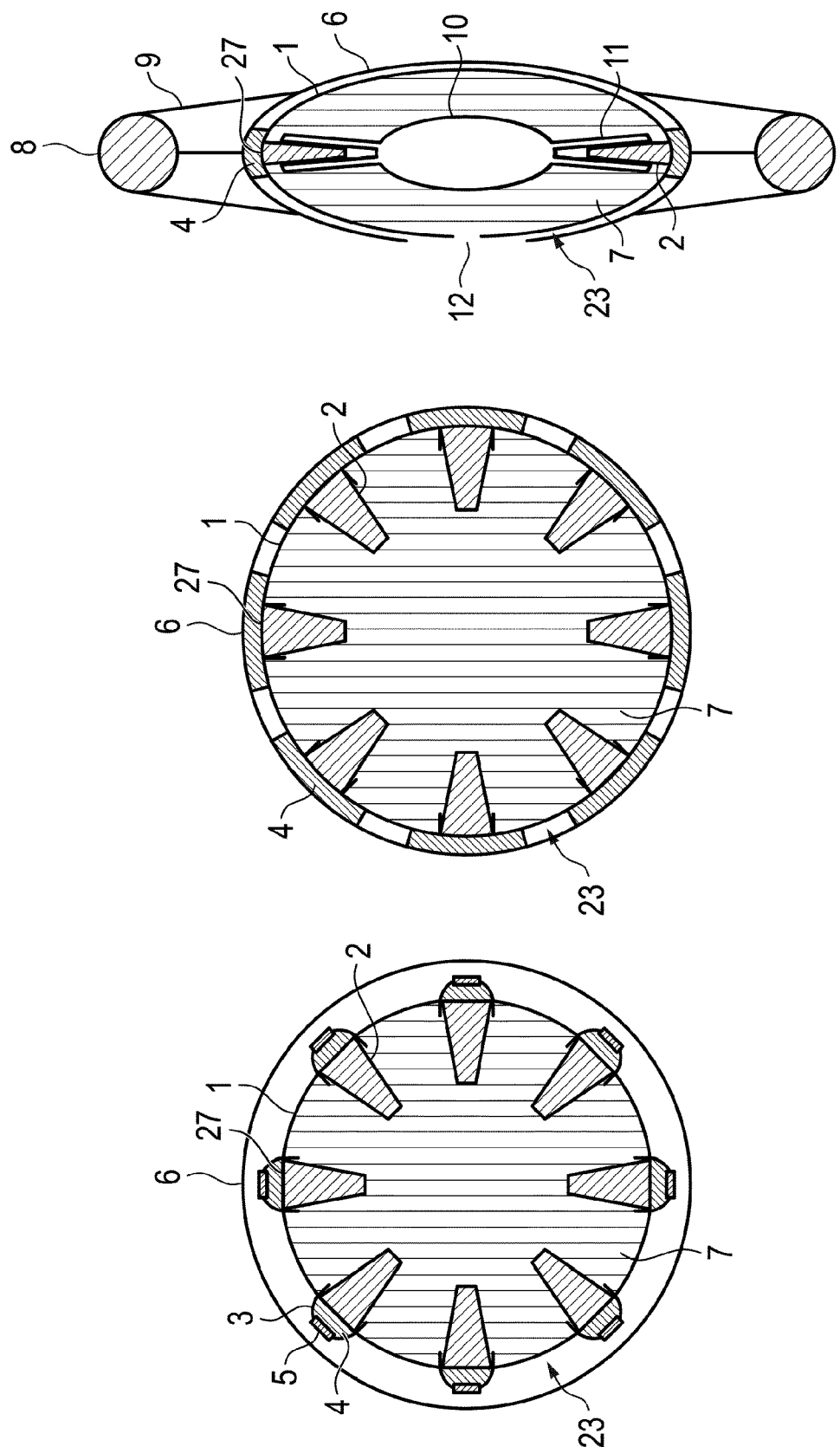
FIG. 1 shows a section through an eye with a first embodiment according to the invention of an eye implant at three different times, the first time being depicted to the left, the second time being depicted in the center and the third time being depicted to the right, with the section at the third time being disposed perpendicular to the sections at the first time and the second time.

As is evident from FIG. 1, an eye implant 23 according to a first embodiment comprises a lens sheath 1, a plurality of reservoirs 3 and at least two adapters 2. The lens sheath 1 is embodied to be inserted into a capsular bag 6 of an eye.

Moreover, the lens sheath 1 delimits a cavity in its interior and comprises a through hole 18 (only depicted in FIG. 3), via which the cavity is accessible from outside of the lens sheath 1. Moreover, the lens sheath 1 is elastic. The reservoirs 3 are fastened to the lens sheath 1 and project from the lens sheath 1 to the outside. Moreover, the reservoirs 3 have an adhesive 4 in their interior and are embodied to dispense the adhesive 4 when pressed against the capsular bag 6. The adapters 2 are fastened to the lens sheath 1 and project from the lens sheath 1 into the interior. Moreover, the adapters 2 are embodied to engage with a respective haptic 11 of an accommodative intraocular lens 10.

Figure 2:
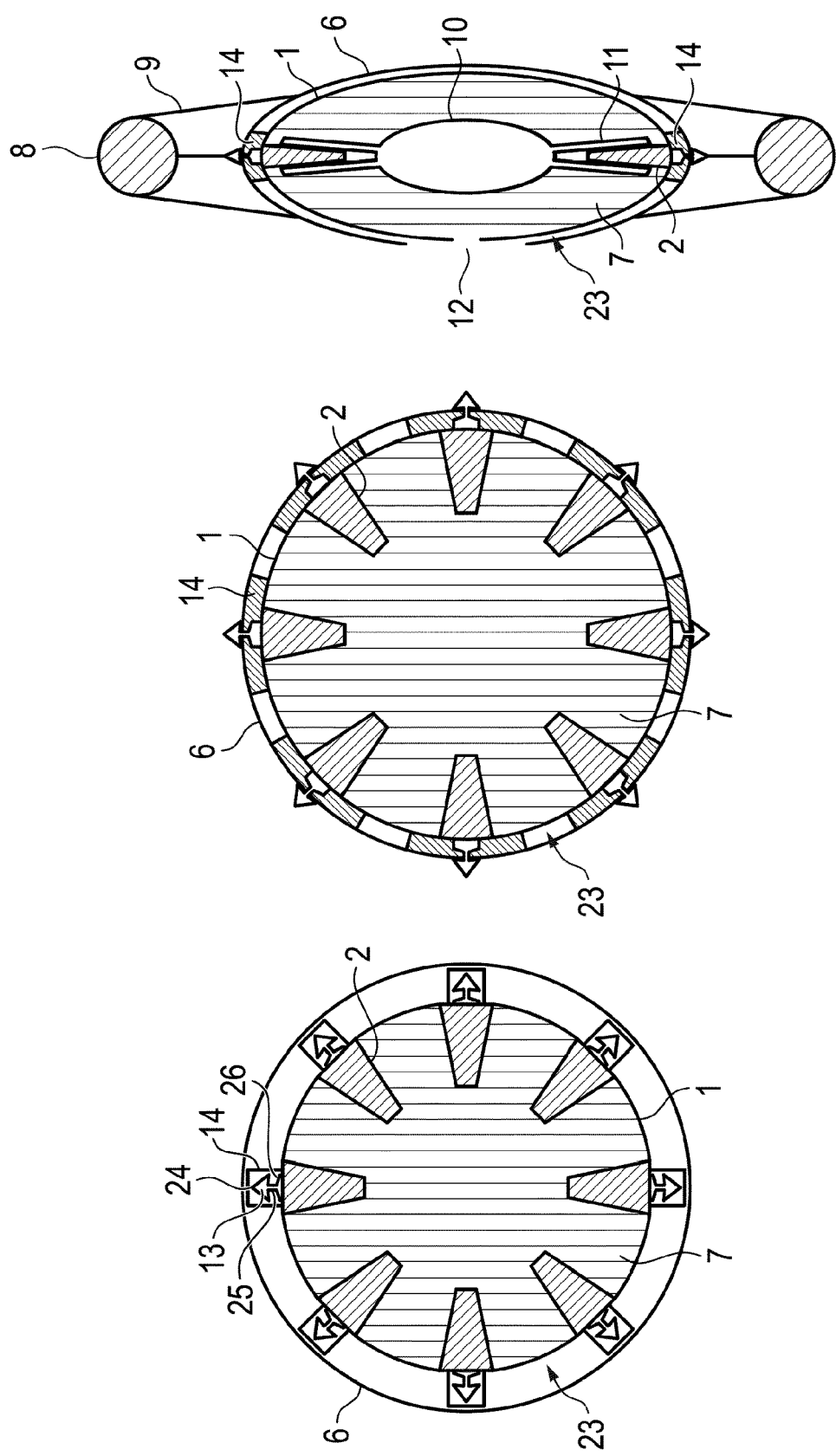
FIG. 2 shows a section through an eye with a second embodiment according to the invention of the eye implant at three different times, the first time being depicted to the left, the second time being depicted in the center and the third time being depicted to the right, with the section at the third time being disposed perpendicular to the sections at the first time and the second time.

As is evident from FIG. 2, an eye implant 23 according to a second embodiment comprises a lens sheath 1, a plurality of protective sheaths 14, a respective barb 13 for each of the protective sheaths 14 and at least two adapters 2. The lens sheath 1 is embodied to be inserted into a capsular bag 6 of an eye. Moreover, the lens sheath 1 delimits a cavity in its interior and comprises a through hole 18, via which the cavity is accessible from outside of the lens sheath 1. Moreover, the lens sheath 1 is elastic. The protective sheaths 14 are fastened to the lens sheath 1 and project from the lens sheath 1 to the outside. Each barb 13 is encapsulated in the interior of the associated protective sheath 14, is connected to the lens sheath 1 and projects from the lens sheath 1 to the outside. Moreover, when the barb 13 is pressed against the capsular bag 6, each barb 13 is embodied to pierce the associated protective sheath 14 and catch in the capsular bag 6. The adapters 2 are fastened to the lens sheath 1 and project from the lens sheath 1 into the interior. Further, the adapters 2 are embodied to engage with a respective haptic 11 of an accommodative intraocular lens 10.

FIGS. 1 and 2 show the eye implant 23 arranged in the capsular bag 6 at three different times, the first time being depicted to the left, the second time being depicted in the center and the third time being depicted to the right. The cavity of the lens sheath 1 is filled with an operating fluid 7, which was introduced into the cavity via the through hole 18, at the first time. Even more operating fluid 7 has been introduced into the cavity at the second time, as a result of which the lens sheath 1 is stretched more than at the first time. According to the first embodiment, this results in the reservoirs 3 being pressed onto the capsular bag 6, as a result of which the reservoirs 3 dispense the adhesive 4 and the eye implant 23 is consequently adhesively bonded to the capsular bag 6. The eye implant 23 adhesively bonded to the capsular bag 6 is depicted at the second time. By virtue of the lens sheath 1 being stretched further, the barb 13 is pressed against the capsular bag 6 according to the second embodiment, as a result of which the barb 13 pierces the protective sheath 14 and catches in the capsular bag 6. The eye implant 23 with the barb 13 caught in the capsular bag 6 is depicted at the second time. What is shown at the third time is that an insertion opening 12 can be introduced into the capsular bag 6, the accommodative intraocular lens 10 being introducible into the cavity via said insertion opening. In addition to the capsular bag 6, the ciliary muscle 8 of the eye and the zonular fibers 9 of the eye are depicted. A state is depicted in which the ciliary muscle 8 has stretched the capsular bag 6 by way of the zonular fibers 9, and hence has deformed the accommodative intraocular lens 10. It is conceivable for the reservoirs 3 or the barbs 13 to all be arranged in one plane. In this case, it is moreover conceivable for this plane to be disposed in the capsular bag 6 in such a way that it is located in the equatorial plane of the crystalline lens of the eye.

FIG. 1 shows that the reservoirs 3 can each have a predetermined breaking point 5, the latter being embodied to be opened when the reservoirs 3 are pressed against the capsular bag 6. In this case, the predetermined breaking points 5 can be dimensioned such that they tear at a first pressure as occurs when the reservoirs 3 are pressed against the capsular bag 6 but do not tear at a second pressure which is lower than the first pressure and which occurs when the eye implant 23 is pressed through a cannula of an injector. A person skilled in the art can conduct experiments which they can use to determine how the predetermined breaking points 5 have to be dimensioned to this end. To this end, they can produce the eye implants 23 with differently dimensioned predetermined breaking points 5 and can expose these to the first pressure and the second pressure.

As an alternative to the predetermined breaking point 5, it is conceivable for the reservoirs 3 to each have a reservoir opening which is embodied to allow the adhesive 4 to pass when the reservoirs 3 are pressed against the capsular bag 6. To this end, the reservoir openings may for example be dimensioned in such a way that they are too small to allow an adhesive 4 to pass before they are pressed against the capsular bag 6, but when they are pressed against the capsular bag 6, the reservoirs 3 with the reservoir openings are stretched in such a way that the adhesive 4 can pass through the reservoir openings.

FIG. 1 shows that the lens sheath 1 can have a sheath opening 27 for each of the reservoirs 3 and one of the adapters 2 which is in contact with the adhesive 4 can be arranged at each of the sheath openings 27. In this case, it is conceivable that, when the cavity is filled by the operating fluid 7 in such a way that the reservoirs 3 are pressed against the capsular bag 6, the adapter 2 presses against the adhesive 4 in such a way that the adhesive 4 is pushed out of the reservoir opening or causes the predetermined breaking point 5 to tear. Moreover, it is evident from FIG. 1 that the reservoir 3 can extend through the sheath opening 27 into the interior of the lens sheath 1. Consequently, the adapter 2 can be connected particularly easily to the reservoir 3 such that no adhesive 4 can reach into the interior of the lens sheath 1.

FIG. 2 shows that each of the barbs 13 can extend through the lens sheath 1 and can be fastened to one of the adapters 2. Moreover, the barb 13 can comprise a barb tip 24, a shaft 25 and an anchor 26, with the barb tip 24 being arranged at one longitudinal end of the shaft 25 and the anchor 26 being arranged at another longitudinal end of the shaft 25, said anchor being able to be fastened to the adapter 2. In this case, the anchor 26 may be arranged within the interior of the lens sheath 1 and the barb tip 24 may be arranged outside of the lens sheath 1. In this case, either the anchor 26 or the shaft 25 may extend through the lens sheath 1.

Figure 3:
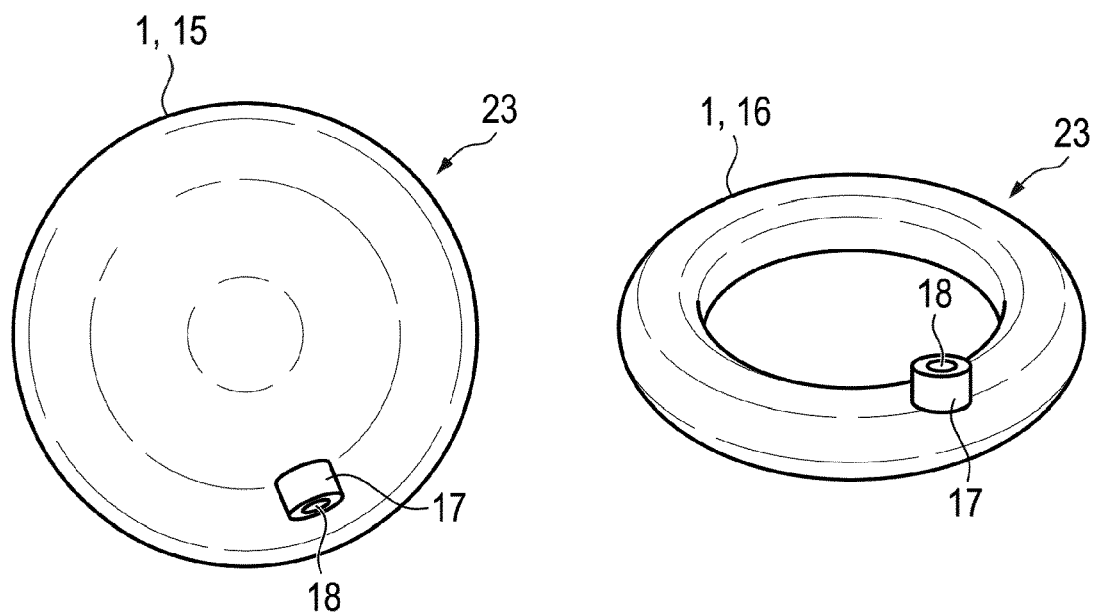
FIG. 3 shows a plan view of two different embodiments of a lens sheath of the eye implant, the lens sheath having a lens sheath swelling.
Figure 4:
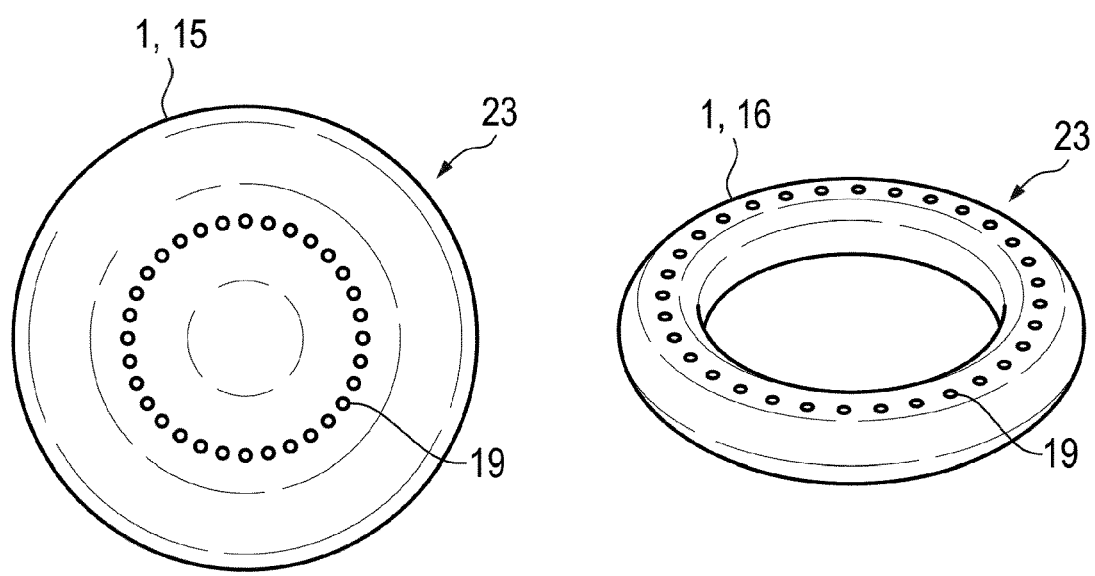
FIG. 4 shows a plan view of two different embodiments of a lens sheath of the eye implant, the lens sheath having a predefined sheath breaking point.

As is evident from FIG. 3 or 4, the lens sheath 1 can be discus-shaped 15 or toroidal 16, with the discus-shaped 15 embodiment in each case being depicted to the left and the toroidal 16 embodiment in each case being depicted to the right. By way of example, the toroidal 16 embodiment may have arisen by the rotation of a surface about an axis of rotation, the surface being located completely within a plane in which the axis of rotation is also located. By way of example, it is conceivable for the surface to have the shape of a circle, with however other shapes, for example an ellipse, also being conceivable.

FIG. 3 shows that the lens sheath 1 may have a lens sheath swelling 17 which is arranged around the through hole 18. The lens sheath 1 may also comprise a valve which contains the through hole 18. In this case, the lens sheath swelling 17 may be part of the valve. This applies both to the discus-shaped 15 embodiment and to the toroidal 16 embodiment.

As is evident from FIG. 4, the lens sheath 1 may have a predetermined sheath breaking point 19. The insert opening 12 can be formed by opening the predetermined sheath breaking point 19. By way of example, the predetermined sheath breaking point 19 can be a perforation. By way of example, the predetermined sheath breaking point 19 may have the form of a closed curve, as is also depicted for both embodiments according to FIG. 4. The lens sheath 1 arranged within the predetermined breaking point 19 can thus be removed from the capsular bag 6 in the case of the discus-shaped 15 embodiment, allowing the amount of material remaining in the capsular bag 6 to be reduced. When the lens sheath swelling 17 is provided, it is consequently advantageous to provide the lens sheath swelling 17 within the predetermined breaking point 19 in order to remove a particularly large amount of material from the capsular bag 6. In the case of the toroidal 16 embodiment, the predetermined sheath breaking point 19 may be provided on an end side of the lens sheath 1, as is also depicted in FIG. 4. Alternatively, it is conceivable for the predetermined sheath breaking point 19 to be provided on the inner side of the lens sheath 1. Alternatively, it is conceivable for the predetermined breaking point 19 to have the form of a line which has a start point and an endpoint and which may be straight and/or curved.

Figure 5:
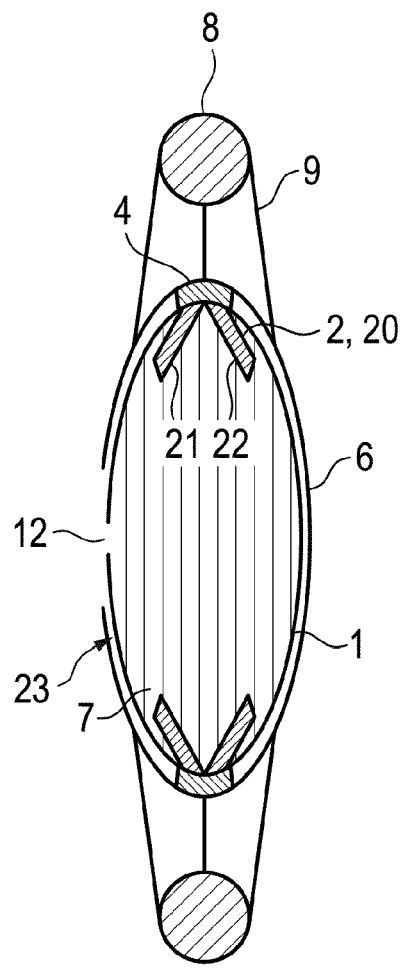
FIG. 5 shows a section through an eye with an embodiment of the eye implant, in which an adapter of the eye implant has a first adapter arm and a second adapter arm.

FIG. 5 shows that each of the adapters 2 can be designed as an open adapter 20 and can comprise a first adapter arm 21 and a second adapter arm 22 which are embodied such that the haptic 11 engages therebetween with the first adapter arm 21 and the second adapter arm 22. The first adapter arm 21 and the second adapter arm 22 are arranged in V-shaped fashion, with the distance between the first adapter arm 21 and the second adapter arm 22 becoming ever longer, the further the first adapter arm 21 and the second adapter arm 22 project inward.

The operating liquid 7 can contain a lubricant and/or a physiological saline solution or can consist of the lubricant and/or the physiological saline solution. The lubricant can be an ophthalmic viscoelastic device (OVD).

LIST OF REFERENCE SIGNS

1 Lens sheath
2 Adapter
3 Reservoir
4 Adhesive
5 Predetermined breaking point
6 Capsular bag
7 Operating fluid
8 Ciliary muscle
9 Zonular fibers
10 Accommodative intraocular lens
11 Haptic
12 Insertion opening
13 Barb
14 Protective sheath
15 Sphere
16 Torus
17 Lens sheath swelling
18 Through hole
19 Predetermined sheath breaking point
20 Open adapter
21 First adapter arm
22 Second adapter arm
23 Eye implant
24 Barb tip
25 Shaft
26 Anchor
27 Sheath opening

The invention claimed is:

1. An eye implant having:
a lens sheath which is sized and configured for insertion in a capsular bag of an eye, is elastic, delimits a cavity in its interior and has a through hole via which the cavity is accessible from outside of the lens sheath, and is discus-shaped or toroidal,
a plurality of reservoirs which are fastened to the lens sheath, project from the lens sheath to the outside, have an adhesive in their interior and are sized and configured to dispense the adhesive when pressed against the capsular bag, and
at least two adapters which are fastened to the lens sheath, project from the lens sheath into the interior, and are sized and configured to engage with a respective haptic of an accommodative intraocular lens,
wherein each of the adapters comprises a first adapter arm and a second adapter arm which are sized and configured such that the haptic engages therebetween, and
wherein the lens sheath comprises capsular-bag-contacting surfaces.

2. The eye implant as claimed in claim 1, wherein the reservoirs each have a predetermined breaking point which is embodied to be opened when the reservoirs are pressed against the capsular bag, or wherein the reservoirs each have a reservoir opening which is embodied to allow the adhesive to pass when the reservoirs are pressed against the capsular bag.

3. The eye implant as claimed in claim 1, wherein the lens sheath has a sheath opening for each of the reservoirs and one of the adapters which is in contact with the adhesive is arranged at each of the sheath openings.

4. The eye implant as claimed in claim 1, wherein the lens sheath has a valve which contains the through hole.

5. The eye implant as claimed in claim 1, wherein the lens sheath has a predetermined sheath breaking point.

* * * * *

UNITED STATES PATENT AND TRADEMARK OFFICE
CERTIFICATE OF CORRECTION

PATENT NO. : 11,678,979 B2
APPLICATION NO. : 17/784049
DATED : June 20, 2023
INVENTOR(S) : Jan Buchheister et al.

It is certified that error appears in the above-identified patent and that said Letters Patent is hereby corrected as shown below:

On the Title Page

In Column 1, item (73), Assignee, Line 1, delete "CARL ZEiSS MEDITEC AG," and insert -- CARL ZEISS MEDITEC AG, --, therefor.

Signed and Sealed this
Seventh Day of November, 2023

Katherine Kelly Vidal
*Director of the United States Patent and Trademark Office*